United States Patent
Wang et al.

(10) Patent No.: US 7,465,453 B2
(45) Date of Patent: Dec. 16, 2008

(54) POLYPEPTIDE FRAGMENTS OF CKLF1

(75) Inventors: Ying Wang, Beijing (CN); Yingmei Zhang, Beijing (CN); Wenling Han, Beijing (CN); Dalong Ma, Beijing (CN); Yanan Liu, Beijing (CN); Caihua Yin, Beijing (CN); Linjie Tian, Beijing (CN); Dan Li, Beijing (CN)

(73) Assignee: Peking University

( * ) Notice: Subject to any disclaimer, the term of this patent is extended or adjusted under 35 U.S.C. 154(b) by 0 days.

(21) Appl. No.: 11/810,590

(22) Filed: Jun. 6, 2007

(65) Prior Publication Data

US 2007/0292443 A1    Dec. 20, 2007

Related U.S. Application Data

(63) Continuation-in-part of application No. PCT/CN2005/002179, filed on Dec. 14, 2005.

(30) Foreign Application Priority Data

Dec. 14, 2004   (CN)   ........................... 200410098627

(51) Int. Cl.
  *A61K 38/10*   (2006.01)
  *A61K 38/16*   (2006.01)
  *C07K 14/435*  (2006.01)
  *C07K 7/08*    (2006.01)
  *C07H 21/04*   (2006.01)

(52) U.S. Cl. .................... 424/185.1; 530/300; 530/324; 530/326; 514/12; 514/13

(58) Field of Classification Search ........................ None
See application file for complete search history.

(56) References Cited

U.S. PATENT DOCUMENTS 6,800,454 B2 * 10/2004 Ma et al. .................... 435/69.1
7,365,171 B2 *  4/2008 Ma et al. .................... 530/399
2002/0001828 A1  1/2002 Ma et al.
2004/0077835 A1  4/2004 Offord et al.
2005/0124043 A1  6/2005 Ma et al.

FOREIGN PATENT DOCUMENTS

CN    1244584 A    2/2000
CN    1441808 A    9/2003
CN    1464057 A   12/2003

OTHER PUBLICATIONS

Wang et al. Two C-terminal peptides of human CKLF1 interact with the chemokine receptor CCR4. Int J Biochem Cell Biol 40(5): 909-919, 2008.*
Wang et al. Chemokine-like factor 1 is a functional ligand for CC chemokine receptor 4 (CCR4). Life Sci 78:614-621, 2006.*
Tan et al. Chemokine-like factor 1, a novel cytokine, contributes to airway damage, remodeling and pulmonary fibrosis. Chin Med J 117(8): 1123-1129, 2004.*
Ke et al. Effects of novel human chemokine-like factor 1 (CKLF1) on bone marrow hematopoietic stem cell/progenitor cell in vitro. Zhonghua Xue Ye Xue Za Zhi 23(6): 301-303, 2002.*
Han W et al, "Molecular cloning and characterization of chemokine-like factor 1 (CKLF1), a novel human cytokine with unique structure and potential chemotactic activity", Biochemical Journal (2001), pp. 127-135, vol. 357, No. 1.

* cited by examiner

*Primary Examiner*—Bridget E Bunner
(74) *Attorney, Agent, or Firm*—Yi Li

(57) ABSTRACT

Polypeptides having an amino acid sequence of SEQ ID NO: 2, and having amino acid residues 9 to 27 of SEQ ID NO: 2 are disclosed, which are together named C-terminal polypeptides of CKLF1. Also disclosed is a pharmaceutical composition containing a therapeutically effective amount of the CKLF1 C-terminal polypeptide and pharmaceutically acceptable salts, carrier or excipient. Further disclosed are the polynucleotides encoding the C-terminal polypeptides of CKLF1, and vectors and host cells containing the polynucleotides; the in vitro assays for detecting the expression level of the polypeptide or polynucleotide in a test sample; and the monoclonal or polyclonal antibodies against the polypeptides or active fragments thereof. The polypeptides of the present invention can be pharmaceutically used for treating the HIV infection, allergic disease, allograft rejection, diseases in brain and autoimmune diseases.

8 Claims, 9 Drawing Sheets

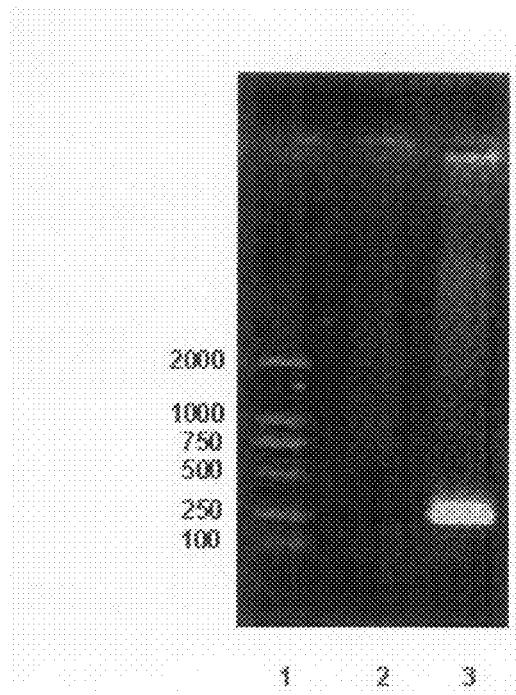
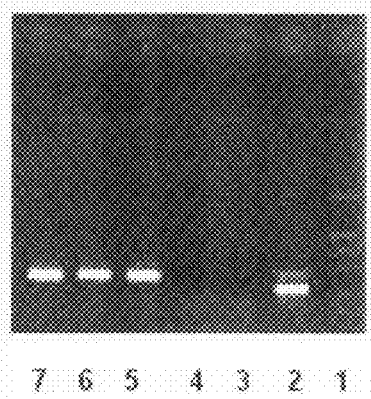
Fig. 1     Fig. 2
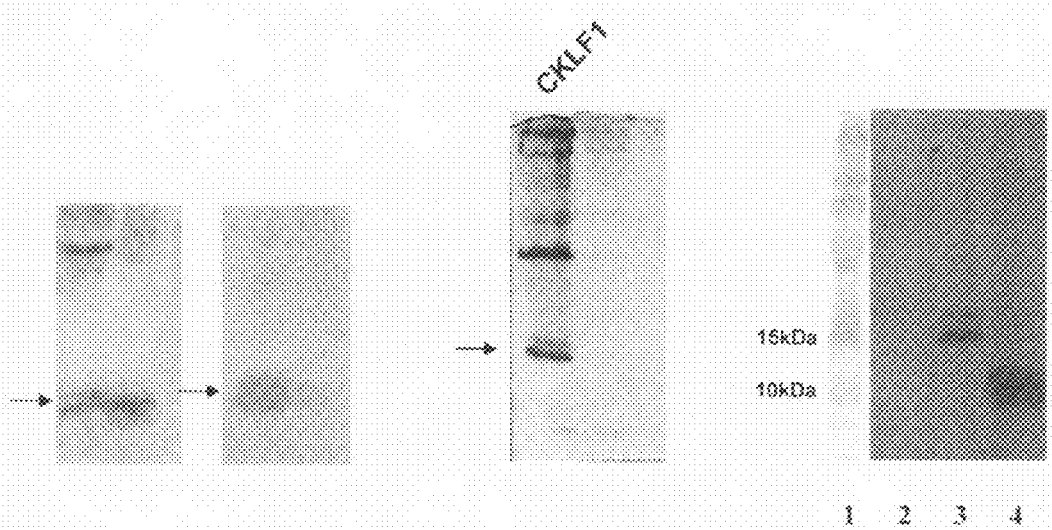
Fig. 3A    Fig. 3B    Fig. 4    Fig. 5

POLYPEPTIDE FRAGMENTS OF CKLF1

CROSS REFERENCE TO RELATED APPLICATION

This application is a continuation-in-part of PCT patent application No. PCT/CN2005/002179, filed on Dec. 14, 2005, which claims the priority of Chinese patent application No. 200410098627.1, filed on Dec. 14, 2004. All prior applications are herein incorporated by reference in their entirety.

FIELD OF THE INVENTION

The present invention is related to genetic engineering technology; especially it relates to polypeptides with multiple functions and polynucleotide encoding such polypeptides, including the vectors and host cells concerning the polynucleotide; and the applications of the polypeptides.

BACKGROUND OF THE INVENTION

The superfamily of chemokine, which has chemotactic effects, belongs to cytokine. It plays an important role in immune defense, immunoregulation, inflammation, the proliferation and differentiation of stem-cells. At present, chemokine has been one of the hot points all over the world. The present inventors, by using suppression subtractive hybridization (SSH) technique, identified and cloned CKLF1 gene, a novel human cytokine with chemotactic effects, from a cDNA library derived from U937 cell line stimulated by phytohemagglutinin (PHA). The open reading frame of CKLF1 cDNA encodes a protein of 99 amino acid sequences. Its GeneBank access number is AF096895. It displayed chemotactic activities in a wide spectrum both in vitro and in vivo. Especially one in vivo study showed that the intramuscular injection of CKLF1 plasmid DNA into BALB/c mice caused inflammation in the lung, which mimicked the phenomena observed in chronic persistent asthma, an allergic lung inflammation. CKLF1 has been described in Chinese patent No. 99107284.7 and corresponding PCT Application No. PCT/CH00/00026 (International Publication number of WO 00/69910). Based on CKLF1, the present inventors obtained new polypeptides of the present invention.

BRIEF DESCRIPTION OF THE DRAWINGS

FIG. 1 shows the detection of hCKLF1-myc in the chromosome of S2 cells stably transfected with pMT/V5HisAhCKLF1-myc using PCR with hCKLF1 primers (SEQ ID NO: 6, SEQ ID NO: 7). Lane 1 is DL2000 DNA molecular-mass standards (Takara); Lane 2, the PCR template is the chromosome of S2 cells stably transfected with pMT/V5HisA; Lane 3, the PCR template is the chromosome of S2 cells stably transfected with pMT/V5HisAhCKLF1-myc.

FIG. 2 shows the detection of hCKLF1-myc expression in S2 cells stably transfected with pMT/V5HisAhCKLF1-myc in the mRNA level using RT-PCR. Lane 1 is DL2000 DNA molecular-mass standards (Takara); lane 2, 3, 4 are the RT-PCR templates of the total RNA from S2 cells stably transfected with pMT/V5HisA, pMT/V5HisAhCKLF1-myc, and untransfected S2 cells, respectively, using hCKLF1 primers (p1, p2); lane 5, 6, 7 are the RT-PCR templates of the total RNA from S2 cells stably transfected with pMT/V5HisA, pMT/V5HisAhCKLF1-myc, and untransfected S2 cells, respectively, using G3PDH primers (p1, p2) as an internal control.

FIGS. 3A and 3B show the detection of hCKLF1-myc expression in S2 cells stably transfected with pMT/V5HisAhCKLF1-myc in the protein level using Western Blotting. In FIG. 3A, the blot was incubated with rabbit polyclonal anti-hCKLF1 peptide antibody and secondary HRP-labeled goat anti-rabbit antibody, and two specific bands with the molecular weight of 8-10 kDa appeared. In FIG. 3B, the blot was incubated with monoclonal anti-Myc antibody and secondary HRP-labeled goat anti-mouse antibody, and the specific band with a molecular weight of 8-10 kDa appeared.

FIG. 4 shows that the purified CKLF1-myc protein was migrated on SDS-PAGE. The gel was stained with Coomassie blue. The arrow indicates CKLF1-myc protein.

FIG. 5 shows that the purified protein samples were separated by SDS-PAGE (15%), transferred to a PVDF filter and detected using Western Blotting. Lane 1 is the protein molecular-mass standards; lane 2 is a pMT (mock)-transfected supernatant; lane 3 is a cell lysate stably transfected with pMT/V5HisAhCKLF1-myc; and lane 4 is a pMT/V5HisAhCKLF1-myc-transfected supernatant.

FIG. 6A shows CKLF1 C19 peptide and FIG. 6B shows CKLF1 C27 peptide.

In FIG. 7A, cells were first stimulated with 100 nM TARC (a-b) and secondly stimulated with 167 nM C27 (c-d); in FIG. 7B, cells were first stimulated with 167 nM C27 (a-b) and secondly stimulated with 100 nM TARC (c-d); in FIG. 7C, cells were first stimulated with 100 nM TARC (a-b) and secondly stimulated with 167 nM C19 (c-d); in FIG. 7D, cells were first stimulated with 167 nM C19 (a-b) and secondly stimulated with 100 nM TARC (c-d); in FIG. 7E, cells were first stimulated with 100 nM RANTES (a-b) and secondly stimulated with 167 nM C27 (c-d); in FIG. 7F, cells were first stimulated with 167 nM C27 (a-b) and secondly stimulated with 100 nM RANTES (c-d); in FIG. 7G, cells were first stimulated with 100 nM RANTES (a-b) and secondly stimulated with 167 nM C19 (c-d); and in FIG. 7H, cells were first stimulated with 167 nM C19 (a-b) and secondly stimulated with 100 nM RANTES (c-d).

In FIG. 8A, cells were transiently transfected with CCR4 expression plasmid, and in FIG. 8B, cells were transiently transfected with CCR5 expression plasmid.

In FIG. 9A, chemotaxis of HEK293 cells transfected with CCR4. HEK293/CCR4 cells were pre-incubated in the absence or presence of CKLF1 C-terminal peptides, TARC or PTX for 30 min; In FIG. 9B, HEK293/CCR5 cells were pre-incubated in the absence or presence of CKLF1 C-terminal peptides, RANTES or PTX for 30 min, wherein M is RPMI-1640; T is TARC; 27 is C27; 19 is C19; P is PTX, and R is RANTES.

DETAILED DESCRIPTIONS OF THE INVENTION

Figure 6A:
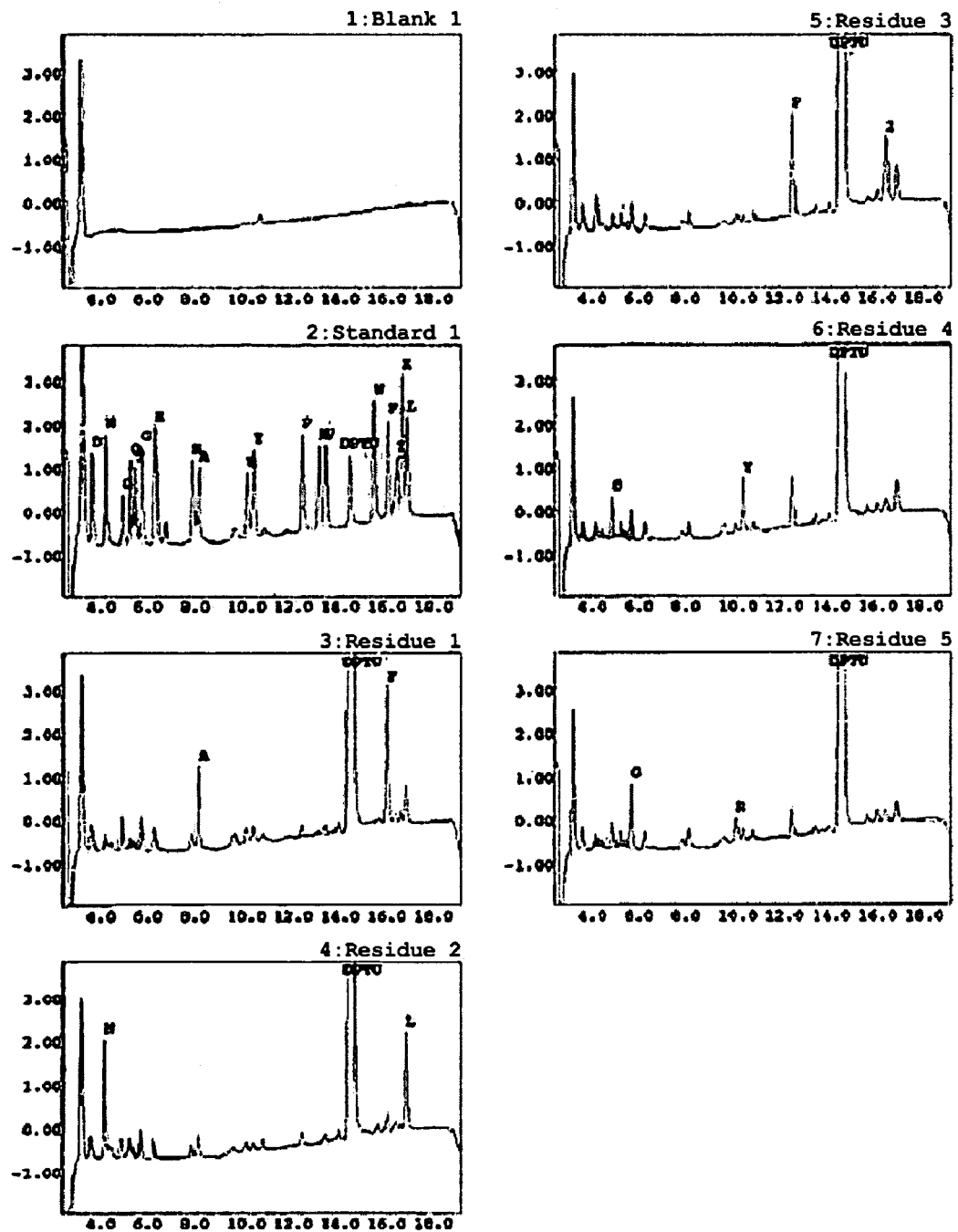
FIGS. 6A and 6B show the results of NH2-Terminal Amino Acid Sequencing of the purified CKLF1-myc protein. The purified CKLF1-myc protein was separated by SDS-PAGE (15%), transferred to a PVDF filter and subjected to NH2-Terminal Amino Acid Sequencing.

The present inventors established CKLF1 protein expressional system in *drosophila,* and then obtained the recombined protein CKLF1, which still displayed chemotactic activities in leukocytes. Using SDS-PAGE, the band of CKLF1 was detected, and after the N-terminal amino acid sequencing, two secretory polypeptides of CKLF1, named polypeptides C19 and C27, were obtained. The present inventors detected that CCR4 and CCR5 were the functional receptors of CKLF1. Then the C19 and C27 were chemically synthesized and the present inventors found that CCR3, CCR4, CCR5, and CCR6 were the functional chemokine receptors of C19 and C27. The receptors could be stimulated or antagonized by C19 and C27. C19 inhibited allergic inflammation. For example, in the prevention and treatment of HIV infection, C19 and C27 could antagonize the binding of HIV to the receptors. Because they could be chemically synthesized and could antagonize the corresponding receptors, C19 and C27 may have much more application prospect in the prevention and treatment of HIV infection, transplant rejection, brain disease, autoimmune disease or the therapy of allergic disease, than CKLF1.

Therefore, one aspect of the present invention relates to one kind of polypeptide.

Another aspect of the present invention relates to one kind of polynucleotide.

Another aspect of the present invention relates to vectors into which the nucleic acid sequence encoding the polypeptides of the present invention is cloned.

Another aspect of the present invention relates to host cells into which the recombinant vectors mentioned above are transducted, transfected, or transformed.

Another aspect of the present invention relates to one drug compound, which comprises of the polypeptide, polynucleotide, vectors, host cells, and one or one more salt compatible with the drug, or carrier or excipient.

Another aspect of the present invention relates to the application of the polypeptide or polynucleotide of the present invention in the invention of the drug which can prevent from and cure HIV infection, allergic disease, transplant rejection, brain disease, and autoimmune disease.

Still another aspect of the present invention relates to a method of detecting whether the expression levels of the polypeptide or polynucleotide of the present invention changed in the tested samples.

Yet another aspect of the present invention relates to monoclonal or polyclonal antibodies of the polypeptide of the present invention.

One aspect of the present invention relates to one kind of polypeptide, it includes a polypeptide whose amino acid sequence is shown as SEQ ID NO:2, and amino acid residues 9 to 27 of SEQ ID NO: 2; and the polypeptide which is 80% homologous to the polypeptide mentioned above.

The polypeptide as shown in SEQ ID NO: 2, named C27 in the present invention, is the sequence of C-terminal 27 amino acid residues of CKLF1. The amino acid residues 9 to 27 of SEQ ID NO: 2, named C19 in the present invention, is the sequence of C-terminal 19 amino acid residues of CKLF1. C27 and C19 are herein referred to as CKLF1 C-terminal polypeptides. The present invention also includes the polypeptides which are 80%, and preferably more than 80%, homologous to C27 and C19, and have the same, similar or different biological functions; the polypeptides which have the same or similar biological functions with C27 and C19 are preferential.

The CKLF1 C-terminal polypeptides in the present invention can be natural, synthesized, semi-synthesized, or recombined. They can be synthesized using Applied Biosystem synthesizer or Pioneer peptide synthesizer by the methods as Steward and Young described in Steward, J. M. and Young, J. D., *Solid Phase Peptide Synthesis,* 2nd Ed., Pierce Chemical Company, Rockford, I11, (1984).

The polypeptides can also be obtained from the host cells, with recombined DNA encoding the polypeptides of the present invention, using genetic engineering technology. The details are shown in Examples 1-4.

The CKLF1 C-terminal polypeptides can also be obtained from the polynucleotide encoding the polypeptides of the present invention. For example the polynucleotide sequence can be directly inserted to the expression vectors, then after the expression and purification, the polypeptides will be obtained. Alternatively, using the mRNA derived from the polynucleotide, the polypeptides also can be obtained.

The polypeptides of the present invention can fuse with other polypeptides which often are known, and some of which can be purchased, synthesized or obtained using genetic engineering technology.

The preferential polypeptides in the present invention comprise (1) the polypeptide having the amino acid sequence as shown in SEQ ID NO: 2; or the polypeptide having amino acid residues 9 to 27 of SEQ ID NO: 2; or (2) the polypeptide which is at least 90% homologous to the two polypeptides described in (1), and which has the same biological functions to the two polypeptides described in (1).

Another aspect of the present invention relates to a polynucleotide, the polynucleotide includes (a) the polynucleotide encoding the amino acid sequence of SEQ ID NO:2 or encoding amino acid residues 9 to 27 of SEQ ID NO:2; or (b) the polynucleotide which is at least 80% homologous to the two polynucleotides of (a), wherein the polypeptide encoded by the polynucleotide has the same function to the polypeptide encoded by the polynucleotide of (a).

The amino acid sequence shown in SEQ ID NO: 2 is the sequence of C-terminal 27 amino acid residues of CKLF1 (C27) and the sequence shown in amino acid residues 9-27 of SEQ ID NO: 2 is the sequence of C-terminal 19 amino acid residues of CKLF1 (C19). The polynucleotides provided by this invention can not only code for the terminal peptide of CKLF1, but also add non-coding sequence, such as introns 5' or 3' UTR, etc. It's preferred to provide the sequence with the detached form which is separated from other ingredients. That is what our invention can provide. It has already been separated from not only the proteins originally attached to it, but also the sequences beside it in nature.

Our invention can also provide polynucleotide which has at least 70%, 80%, 85% or 90%, 95% or even 98% homologous to the polynucleotide encoding the C-terminal polypeptide of CKLF1 or fragment thereof.

This is especially for the polynucleotide which can hybridize with the ones encoding the C-terminal polypeptide of CKLF1 in the strict conditions. Herein, the term "the strict conditions" means the sequences must own at least 95% homology with each other. This kind of sequence maybe exist in nature or manmade, including the variation of the allele encoding C-terminal of CKLF1 or the deletion, insertion and replacement form of the polynucleotide encoding C-terminal of CKLF1. The polypeptide encoded by this kind of sequence can be the same with the C-terminal polypeptide of CKLF1 in function, or just similar to it, or totally different from it. However, the polypeptides with the same or similar function are preferred. Therefore, it is preferred to choose the polynucleotides which have at least 80% homology with the ones shown in SEQ ID NO:2 to ensure that the polypeptides encoded by the sequences selected can have the same function with the ones shown in SEQ ID NO:2.

The polynucleotides provided by the present invention can be DNA or RNA, and the DNA can be cDNA, genome DNA, or the manmade DNA. The DNA can be double-strand or single-strand. The single-strand can be the coding or noncoding strand. The noncoding strand mentioned herein can be the complementary sequence shown as in SEQ ID NO:1. It is already known that noncoding strand or just part of it can be used in inhibiting the expression of CKLF1 C-terminal polypeptide in cell. The sequence coding the C-terminal of CKLF1 can be from any species, especially the mammal, including cattle, sheep, pig, mouse, horse, and preferably human.

The polynucleotide sequence shown in SEQ ID NO:1 encodes the polypeptide C27, which comes from human. The nucleotides 25 to 81 of SEQ ID NO: 1 encodes C19, which also comes from human. Therefore, it is preferred to choose the polynucleotide shown in SEQ ID NO:1, or its complementary sequence, or nucleotides 25 to 81 of SEQ ID NO: 1.

Also, another aspect of the present invention relates to genetically engineered vectors, which contain the polynucleotide encoding the C-terminal polypeptide of the present invention. Such vectors can be cloning vectors or expression vectors. Cloning vectors are always employed to construct genomic and cDNA libraries. Cloning vectors always contain two or more marker genes to provide a phenotypic trait for selection of transformant and insert of exogenous DNA. Expression plasmids are employed to study the gene expression, produce useful transcriptional products or proteins, and sometimes construct cDNA libraries. In addition to the characteristics of cloning vectors, the expression vectors also contain appropriate promoter, ribosome binding site and transcription terminator. An appropriate leader sequence can be fused to the upstream of the encoding sequence of polypeptide for the required cellular location of the expressed products. The method for appropriate selection of vectors and promoters, as well as the construction method of the vectors containing the polynucleotide of the present invention and suitable transcriptional and translational elements are known to those of skilled in the art. More specifically, commercial expression vectors for prokaryotic cell use usually comprise a selectable marker, bacterial origin of replication, bacterial promoters such as lacl, T7, PL and trp0, and other genetic elements of the well known cloning vector PBR322 (ATCC 37017). Such commercial vectors include, for example, KK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed. The present invention also contains the GST prokaryotic expression system. Useful vectors for eukaryotic use contain eukaryotic promoters such as CMV and SV40. Such vectors include pMT-hIL-3 (Dalong Ma, Chunhui Di, Jiang Pang, etc. (1991) *High Technology Letters* 11:26-29), pQE-9 (Qiagen), pD10, pNH18A (Stratagene), pKK233-3, pDR540, pRIT5 (Pharmacia), as well as pcDNA3, pCl, pWLNEO, pSG (Stratagene) and pSVL (Pharmacia). In Example 1 of the present invention, the expression plasmid named pCDNA3.1-CKLF1-myc-his6 is constructed by inserting the coding region of CKLF1 into the expression plasmid pCDNA3.1-myc-his6 (Invitrogen). The PCR products are excised with EcoRI+XhoI and subcloned into the EcoRI+XhoI site of the pMT/V5-His A vector (Invitrogen). The resulting recombinant plasmid is designated as pMT/V5-HisA-CKLF1-myc-his6.

Another aspect of the present invention relates to the host cells, containing the polynucleotide encoding the CKLF1 C-terminal polypeptide of the present invention. Representative examples of appropriate hosts are: (i) prokaryotic cells, such as *E. coli, Bacillus, Streptomyces*, etc.; (ii) eukaryotic cells, such as yeast and *Aspergillus*; (iii) insect cells, such as *Drosophila* S2 and SDodoptera Sf9; (iv) animal cells, such as CHO and COS (Gluzman, *Cell* 23:175, 1981). The above-described constructs are introduced into the host cells by various methods. The representatives, but non-limiting examples, include calcium chloride mediated transformation, calcium phosphate transfection, DEAE-Dextran mediated transfection, electroporation, microinjection and particle bombardment, or Gene gun bombardment (Sambrook, J. (1989), *Molecular Cloning, a Laboratory Manual*, Cold Spring Harbor Press; Plainview, N.Y.; Ausubel, F. M. (1989) *Current Protocols in Molecular Biology*, John Wiley & Sons, N.Y.; Hobbs, S. et al., *McGraw Hill Yearbook of Science and Technology* (1992), McGraw Hill, N.Y. 191-196; Engelhard, E. K. et al., *PNAS*, 91:3224-3227; Logan, J. et al., *PNAS*, 81:3655-3659). Following transformation of a suitable host strain and growth of the host strain to an appropriate cell density, the selected promoter is induced by appropriate means (e.g., temperature shift or chemical induction) and cells are cultured for an additional period. Such methods are well known to those skilled in the art. For example, the host cell of XL1-Blue *E. coli.* is used in Example 1 of the present invention and the *Drosophila* S2 cell in Example 2. Calcium chloride transfection is used in both examples. In Example 7, HEK293 cell (ATCC CRL-1573) serves as the host cell and the transfection method is electroporation.

Another aspect of the present invention relates to making drug compounds. Such drug compounds comprise a therapeutically effective amount of the CKLF1 C-terminal polypeptide, the polynucleotide encoding the corresponding CKLF1 C-terminal polypeptide, vectors, host cells containing the above polynucleotide, and one or more pharmaceutically acceptable salts, carrier or excipient. The phrase "pharmaceutically acceptable salt(s)", as used herein, means those salts that are safe for topical or systemic use in animals or humans without excess toxicity, stimulus, allergic reaction, etc. The pharmaceutically acceptable salts of the present invention are the regular ingredients for pharmaceutical use. These salts can be prepared in the final separation and purification of the CKLF C-terminal polypeptide of the present invention, as well as the additional reaction process of the polypeptide with suitable inorganic/organic acid or alkali. The pharmaceutically acceptable carrier or excipient means those nontoxic solid, semisolid or liquid additives such as packing, diluent, encapsulation, etc.

Still further, another aspect of the present invention relates to the pharmaceutical application of CKLF1 C-terminal polypeptide in preventing or curing the HIV infection, allergic disease, allograft rejection, diseases in brain and autoimmune diseases.

Recent studies show that the entry of the human immunodeficiency virus type 1 (HIV-1) into target cells requires the interaction with chemokine receptors, such as CCR3, CCR5, CXCR4, and CX3CR1. The recently developed inhibitors for HIV infection include chemokines encoded by Kaposi's sarcoma-associated herpes virus and HHV-8 vMIP, which can bind to dozens of chemokine receptors so as to inhibit the HIV infection. The modified human chemokine and compounds of small molecule can specifically bind to CCR5 and CXCR4 to inhibit the HIV infection. The CKLF1 C-terminal polypeptide of the present invention can bind to dozens of chemokine receptors which are consistent with the HIV-bound coreceptors (Example 7-8). In addition, the property of human derived polypeptide provides lasting and effective application. Therefore, the CKLF1 C-terminal polypeptides of the present invention is very useful in preventing the spread of HIV-1 following infection.

Atopic dermatitis, asthma and allergic rhinitis are the most common allergic diseases related closely to the migration of Th2 cells, mast cells and eosinophil cells. Use of some chemokine receptor antagonist provides one treatment strategy. CCR3, CCR4, and CCR8 are always expressed on Th2 cells, mast cells and eosinophil cells. Furthermore, CCR5 also relates to the development of asthma. The reliable experiment results of the present invention show that CKLF C-terminal polypeptides are the functional ligand of CCR4 and CCR5. Therefore, CKLF1 C-terminal polypeptides also play an important role in inhibition of allergic diseases.

Studies have shown that CCR5 takes part in the development of diseases in brain and its expression is detected in the activated microglial cell and T cells in brain lesion site of Multiple Sclerosis as well as in the activated microglial cell in the brain lesion site of Alzheimer's disease. Examples 7 and 8 of the present invention indicate that the CKLF C-terminal polypeptide is the ligand of CCR5. Therefore, CKLF C-terminal polypeptides can be used to prevent the lesion caused by chronic inflammation of these diseases.

CCR5 and its ligands also take part in the development of allograft rejection, rheumatoid arthritis and hepatitis C, and CCR6 relates to psoriasis. Examples 7-9 of the present invention indicate that the CKLF C-terminal polypeptide can combine with several above mentioned receptors, which implies that CKLF C-terminal polypeptides can be used to prevent the development of allograft rejection, rheumatoid arthritis, hepatitis and psoriasis.

Some diseases such as autoimmune diseases, allergic diseases and HIV infection relate closely to chemokines and their ligands. Application of antagonists is one of main remedy strategies. The experiments of the present invention indicate that the CKLF1 C-terminal polypeptides, with the ability of binding chemokine receptors and the human derived property, provide promising applications in the treatment of these diseases.

The present invention also relates to in vitro assays for detecting the expression level of the polypeptide or polynucleotide of the present invention in a text sample. Such assays include RT-PCR method and western blotting analysis.

Various well known methods in the art can be used for detecting the expression level of polypeptide or polynucleotide of the present invention. The preferable methods are the RT-PCR for detecting of nucleotide level of the above described polynucleotide and some assays, such as western blotting, using specific monoclonal antibody or polyclonal antibody to detect the protein level of the above described polynucleotide. The test samples can be derived from cells of various origins such as blood, urine, saliva, gastric juice, hair, biopsy, and autopsy. RT-PCR involves two main steps: the RT reaction and PCR amplification. The extracted RNA is first reverse transcribed into cDNA using a reverse transcriptase. The resulting cDNA is used as templates for subsequent PCR amplification using primers specific for the cDNA. The two primers are located on different exons to prevent the contamination of genomic DNA. Western blotting is mainly a three-step procedure: First, separate the proteins (e.g., antigens) using SDS-polyacrylamide gel electrophoresis. This separates the proteins by size. Second, place a nitrocellulose membrane on the gel and, using electrophoresis, drive the protein bands onto the nitrocellulose membrane. Third, incubate the nitrocellulose membrane with the same pattern of separation as the gel with the primary antibody against the protein of interest and then the enzyme-conjugated secondary antibody. The substrate specific for the enzyme is added to visualize the protein band. The conjugated enzymes include horseradish peroxidase (HRP) and alkaline phosphatease (AP), as well as glucoseoxidase, $\beta$-D-galactosidase, urease, etc. HRP is used as the enzyme linked to the secondary antibody in one of the examples of the present invention. Those of skilled in the art are aware that the substrates vary depending on different conjugated enzymes. The substrates specific for HRP include, but are not limited to, OPD, TMB, ABTS, etc. The p-NPP is usually used as the substrate specific for AP, and sometimes, fluorescent substrate, such as 4-methylumbelliferone, is used. The common enzyme-conjugated secondary antibodies are available commercially.

Yet another aspect of the present invention relates to antibodies specific to the CKLF1 C-terminal polypeptides or its antigenic fragments. These antibodies can be, for example, polyclonal or monoclonal antibodies, especially the monoclonal antibody. The antibody specificity refers to that the antibodies can specifically bind to the CKLF1 C-terminal polypeptide of the present invention or its antigenic fragments. The preferred antibody refers to those capable of binding to CKLF C-terminal polypeptide of the present invention, but not other unrelated antigens. No matter whether they inhibit the polypeptide function or not, the antibodies capable of binding to CKLF1 C-terminal polypeptide are included in the present invention. The present invention also include those antibodies being able to specifically bind to proteins or active fragments with at least 86% identity to CKLF1 C-terminal polypeptide of the present invention. The present invention not only include the complete polyclonal or monoclonal antibodies, but also the antibody fragments with immune activity, such as the antibody-binding fragments (Fab) or (Fab)$_2$, antibody heavy and light chains, as well as genetically engineered single chain Fv molecules (Ladner etc., American U.S. Pat. No. 4,946,778) or fused antibodies, for example the humanized antibodies with the binding specificity of mouse antibodies.

For preparation of antibodies of the present invention, the techniques known in the art can be used. For example, the purified CKLF1 C-terminal polypeptides of the present invention or its antigenic fragments can be administered to an animal to generate the polyclonal antibodies. Similarly, cells expressing CKLF1 C-terminal polypeptides of the present invention or its antigenic fragments can be directly injected into an animal to produce antibodies. The preferred monoclonal antibody of the present invention can be produced by hybrioma technology (Kohler, etc., *Nature* 256:495; Kohler, et al., *Eur. J. Immunol.* 6:511, 1976; Hammerling, et al., *In Monoclonal Antibodies and T cell Hybridaomad*, Elsevier, N.Y., 1981). All antibodies of the present invention can be produced by directly injecting an animal with the CKLF1 C-terminal polypeptides, fragments, or their active domains of the present invention. These fragments and active domains can be prepared by recombinant method or protein synthesizer. Antibodies corresponding to the unmodified CKLF1 C-terminal polypeptides can be generated by administering an animal with the CKLF1 C-terminal polypeptides or its fragments produced in prokaryotic cells (e.g., *E. coli*). Antibodies corresponding to the CKLF1 C-terminal polypeptides of posttranscriptional modification (e.g., glycosylation or phosphorylation) can be produced by administering an animal with the CKLF1 C-terminal polypeptides or fragments thereof expressed in eukaryotic cells, such as yeast or mammal cells (e.g., rabbit).

EXAMPLES

Example 1

Construction of pMT/V5-HisA-CKLF1-myc-his6 Fusion Protein Expression Plasmid

The construction of pMT/V5-HisA-CKLF1-myc-his6 plasmid, for expressing CKLF1-myc-his6 fusion protein, is described below.

1. Methods:

The cDNA fragment covering the open reading frame for CKLF1 (SEQ ID NO: 3) was cloned into an expression vector pCDNA3.1-myc-his6 (Invitrogen), and pCDNA3.1-CKLF1-myc-his6 expression plasmid was obtained. The CKLF1 cDNA containing the entire coding region was further obtained by PCR using primers, forward 5'-TGTAATAC-GACTCACTATAG-3' (SEQ ID NO: 4) and reverse 5'-CAT-TGAGTTTAAACGGTCTCGAGCGG-3' (SEQ ID NO: 5), and pCDNA3.1-CKLF1-myc-his6 as template, and then PCR product was treated with EcoR I+Xho I and subcloned into the EcoR I+Xho I site of the pMT/V5-Myc-His A vector downstream of the metallothionein promoter, which was confirmed by DNA sequencing and designated as pMT/V5-HisA-CKLF1-myc-his6. The plasmid was purified by Qiagen 100 and was used to cell transfection.

2. Results:

The sequence of CKLF1 coding region in pMT/V5-HisA-CKLF1-myc-his6 expression plasmid is consistent with SEQ ID NO: 3.

Example 2

Construction of pMT/V5-HisA-CKLF1-myc-his6 Expression Plasmid

1. Methods:

The cultured cells for transfection were prepared by seeding $3 \times 10^6$ S2 cells in a 35 mm plate in 3 ml complete Schneider's *Drosophila* Medium ($1 \times 10^6$ cells/ml) and growing at 28° C. for 16 hours until cells reach a density of $2\text{-}4 \times 10^6$ cells/ml. For cell transfection, the following transfection mixs (per 35 mm plate) were prepared.

In a microcentrifuge tube, the following components were mixed together. This is Solution A.

2 M $CaCl_2$, 36 µl

Recombinant pMT/V5-HisA hCKLF1-myc DNA (19 µg), 19 µl

Selection vector pCoHygro (1 µg), 1 µl

Tissue culture sterile water, bring to a final volume of 300 µl

In a second microcentrifuge tube, 300 µl 2× HEPES-Buffered Saline (HBS) (50 mM HEPES, 1.5 mM Na2HPO4, 280 mM NaCl, pH 7.1) was added. This is Solution B.

Solution A was slowly added to Solution B (dropwise) with continuous vortex until Solution A was depleted. This was a slow process (1 to 2 minutes). The resulting solution was incubated at room temperature for 30 minutes. The solution was mixed and added dropwise to the cells (swirl to mix with each drop). The cells were incubated for 16 hours at 28° C., then the medium containing calcium phosphate solution was removed and the cells were washed twice with complete medium at centrifugation of 1000×g for 2 to 3 minutes. After decanting the medium, fresh medium was added and replated into the same vessel, cells were continued to incubate at 28° C. for 3 days. The cells were centrifuged and resuspended in complete Schneider.s *Drosophila* Medium containing 300 µg/ml of hygromycin-B. Selective medium was replaced every 4 to 5 days until resistant cells start growing out (3 to 4 weeks for hygromycin-B). After 2 weeks more than 98% untransfected cells died. The chromosomes of the resistant cells transfected with pMT/V5-HisA hCKLF1-myc or empty vector were isolated and detected using PCR with hCKLF1 primers (SEQ ID NO: 6, 5'ATG GAT AAC GTG CAG CCG AAA AT 3'; SEQ ID NO: 7, 5'CAA AAC TTC TTT TTT TTC ATG CAC A 3').

Furthermore, the healthy log-phase S2 cells as feeding cells were plated in 96-well plates to $1.1 \times 10^5$/well with the treatment of 300 µg/ml hygromycin-B. The resistant cells transfected with pMT/V5-HisA hCKLF1-myc and selected with hygromycin-B were diluted to $1 \times 10^4$/ml, $1 \times 10^3$/ml, $1 \times 10^2$/ml, $1 \times 10^1$/ml, and the 100 µl of each dilution cells were plated into one 96-well plates with S2 feeding cells in fresh medium containing 10% FBS and 300 µg/ml hygromycin-B, respectively. Cells were continued to incubate at 24° C., with replacement of half of selective medium every 4 to 5 days until resistant cells start growing out and feeding cells died (2 weeks for hygromycin-B). The resistant cells were expanded into 48-well plates and subcultured with two passage to detect hCKLF1-myc in the chromosome of S2 cells stably transfected with pMT/V5HisAhCKLF1-myc using PCR with hCKLF1 primers (SEQ ID NO: 6, SEQ ID NO: 7) and 30 reaction cycles. The cell chromosomes were conventionally isolated with cell lysis buffer, Proteinase K and RNAseA. Then, the total RNA of S2 cells stably transfected with pMT/V5HisAhCKLF1-myc or empty vector was extracted with BODA TRIZOL and was detected with GIBCO-BRL RT-PCR kit.

The positive cloned cells were expanded and induced to test for target protein expression using Western Blotting. Cell lysates were separated on 15% SDS-PAGE and then transferred to PVDF membranes with 1×Caps transfer buffer. After blocking in Tris-buffered saline containing 0.05% Tween-20 (TBS-T) and 5% BSA for 1 hour at room temperature, membranes were incubated with corresponding Anti-c-myc antibody overnight at 4° C. Membranes were then washed with TBS-T three times for 10 minutes and then incubated with secondary HRP-labeled goat anti-rabbit antibody for 1 hour at room temperature. Following another three washes with TBS-T for 10 minutes, the fluorophores on the membrane were detected using ECL Western Blotting Detection kit (Amersham Life Science).

2. Results:

(i). The DNA of hCKLF1-myc could be detected in the chromosome of S2 cells stably transfected with pMT/V5HisAhCKLF1-myc using PCR with hCKLF1 primers (SEQ ID NO: 6, SEQ ID NO: 7). The chromosomes of S2 cells stably transfected with pMT/V5HisA and pMT/V5HisAhCKLF1-myc as template were used, respectively. PCR products were separated by using a 1% agarose gel and identified by ethidium bromide staining. As shown in FIG. 1, Lane 1 was DL2000 DNA molecular-mass standards (Takara); Lane 2, RT-PCR template was the chromosome of S2 cells stably transfected with pMT/V5HisA; Lane 3, RT-PCR template was the chromosome of S2 cells stably transfected with pMT/V5HisAhCKLF1-myc, and a 300 bp band of hCKLF1-myc could be specifically detected in Lane 3.

(ii). hCKLF1-myc expression can be detected in S2 cells stably transfected with pMT/V5HisAhCKLF1-myc in the mRNA level using RT-PCR. As shown in FIG. 2, Lane 1, DL2000 DNA molecular-mass standards (Takara); Lane 2, 3, 4, RT-PCR template was the total RNA from S2 cells stably transfected with pMT/V5HisA, pMT/V5HisAhCKLF1-myc, and untransfected S2 cells, respectively, using hCKLF1 primers (p1, 5'-GCA AGA AGC GGG AAG CCG A-3' (SEQ ID NO: 8), p2, 5'-CAT TGA GTT TAA ACG GTC TCG AGC GG-3'(SEQ ID NO: 5); Lane 5, 6, 7, RT-PCR template is the total RNA from S2 cells stably transfected with pMT/V5HisA, pMT/V5HisAhCKLF1-myc, and untransfected S2 cells, respectively, using G3PDH primers (p1, 5' ACCA-CAGTCCATGCCATCAC 3' (SEQ ID NO: 9), p2, 5' TCCACCACCCTGTTGCTGTA 3' (SEQ ID NO: 10) as an internal control, a 300 bp band of hCKLF1-myc could be specifically detected in Lane 2.

(iii). hCKLF1-myc protein expression could be detected in S2 cells stably transfected with pMT/V5HisAhCKLF1-myc in the protein level using Western Blotting. As shown in FIG. 3A, the blot was incubated with rabbit polyclonal anti-hCKLF1 peptide antibody and secondary HRP-labeled goat anti-rabbit antibody, and two specific bands with the molecular weight of 8-10 kDa appeared. In FIG. 3B, the blot was incubated with monoclonal anti-Myc antibody and secondary HRP-labeled goat anti-mouse antibody, and the specific band with a molecular weight of 8-10 kDa appeared.

Example 3

The Purification of CKLF1-myc Protein

1. Methods:

The positive cloned cells that can express CKLF1-myc protein in Drosophila-SFM (Invitrogen) without hygromycin-B were expanded and induced to produce recombinant CKLF1-myc protein with $CuSO_4$. After 30 hours, the cell supernatants were collected, centrifuged at 2000 rpm for 10 min and 8000 rpm/min for 20 min, respectively, and filtrated through 0.4 μm filters. Then, these cell supernatants were loaded onto a Chelating Sepharose Fast Flow column (Qiagen) equilibrated in the buffer containing 50 mM sodium phosphate (pH 8.0). The column was then washed in phosphate-buffered saline (PBS) buffer and buffers containing 0.5M NaCl, 10, 50 and 500 mM imidazole sequentially.

2. Results:

As shown in FIG. 4, the purified CKLF1-myc protein was migrated on 15% SDS-PAGE. The gel was stained with Coomassie blue. The arrow indicates CKLF1-myc protein.

Example 4

Amino Acid Sequence Determination of Secreted CKLF1-myc Protein

1. Methods:

The positive pool of the purified CKLF1-myc detected by Western blot with the anti-Myc antibody was dialyzed in PBS buffer to remove imidazole and loaded again onto a Ni-NTA Chelating Sepharose Fast Flow column (Qiagen). The column was then washed in buffer (PBS buffer containing 10 mM imidazole (pH 8.0) and 10% glycerol), and CKLF1 eluted in 500 mM imidazole. Then the samples were migrated on 15% acrylamide SDS-PAGE and transferred to PVDF. The bands were detected with 0.1% (w/v) Coomassie Brilliant Blue R-250 in 50% HPLC methanol grade and the two bands with a molecular weight of ~10 kDa were subjected to sequencing by utilizing Applied Biosystems Procise 491 protein sequencer.

2. Results:

As shown in FIG. 5, the purified protein samples were separated by SDS-PAGE (15%), transferred to a PVDF filter and detected using Western Blotting, Lane 1, protein molecular-mass standards; Lane 2, a pMT (mock)-transfected supernatant; Lane 3, a cell lysate stably transfected with pMT/V5HisAhCKLF1-myc; and Lane 4, a pMT/V5HisAhCKLF1-myc-transfected supernatant, indicating that CKLF1-myc protein was secreted.

Figure 6B:
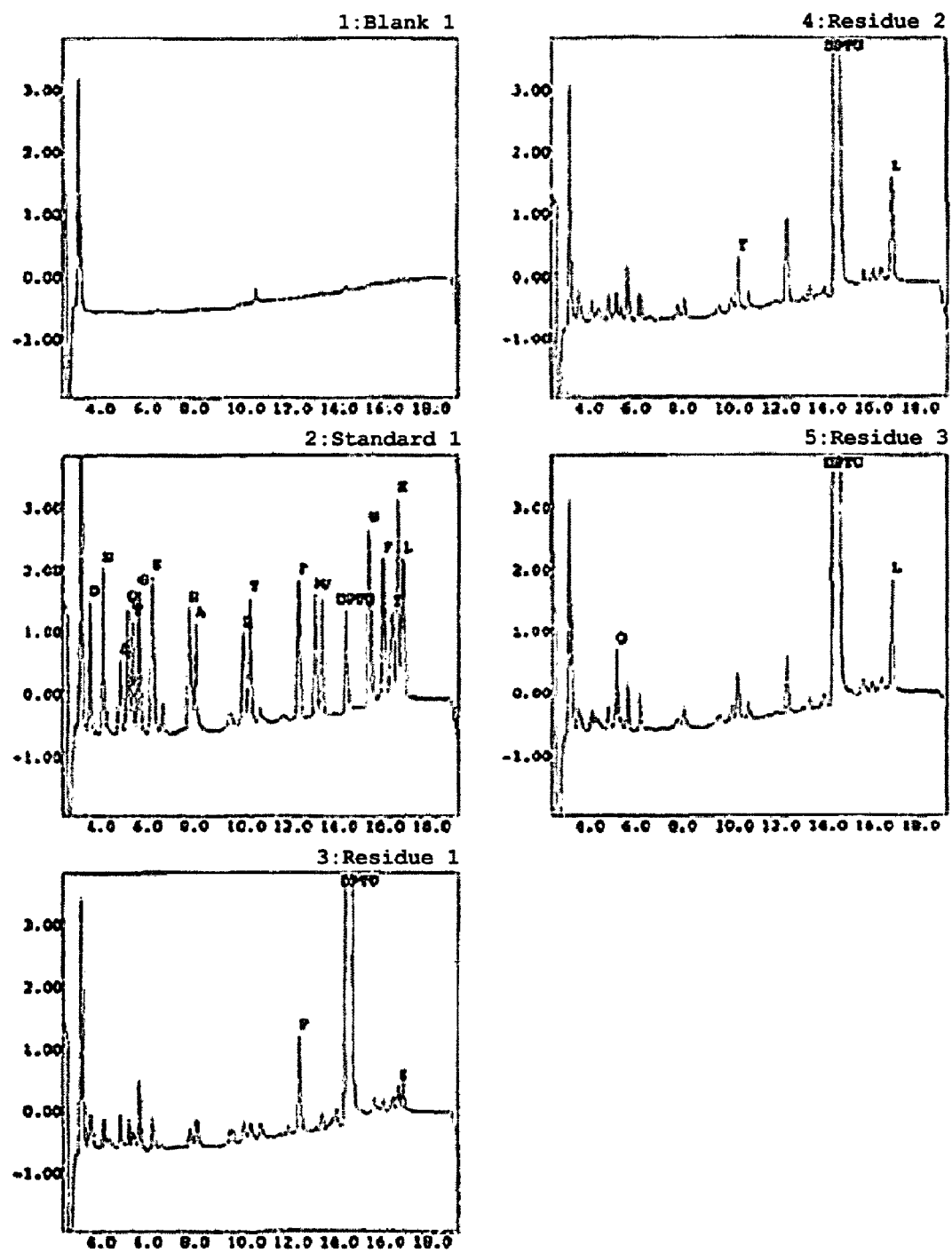

As shown in FIGS. 6A and 6B, the results of NH2-terminal amino acid sequencing of the purified CKLF1-myc protein indicated that the bands included two kinds of $NH_2$-terminal amino acid sequences, A-L-I-Y-R-K-L-L and F-N-P-S-G-P-Y-Q. The purified CKLF1-myc protein was separated by SDS-PAGE (15%), transferred to a PVDF filter and subjected to $NH_2$-Terminal Amino Acid Sequencing. FIG. 6A shows CKLF1 C19 peptide, and FIG. 6B shows CKLF1 C27 peptide.

Example 5

The Amino Acid Sequence Synthesis of Secreted CKLF1 Peptides

1. Methods:

The results of $NH_2$-terminal amino acid sequencing of the purified CKLF1-myc protein indicated that secreted CKLF1 existed in two mature forms, i.e., ALIYRKL LFNPSG-PYQKKPVHEKKEVL (C27) (SEQ ID NO: 2) and FNPSG-PYQKKPVHEKKEVL (C19) (residues 9 to 27 of C27 sequence (SEQ ID NO: 2)). For further functional analyses, the secreted CKLF1 peptides were chemically synthesized in ShenZhen Hybio Engineering Co., Ltd., CN.

2. Results:

The lyophilized CKLF1 peptides was solubilized in PBS buffer with a stock concentration of 1 mg/ml and stored at −80° C.

Example 6

Construction and Expression of Receptor Expression Plasmids

1. Methods:

(i). The Construction of Receptor Expression Plasmids

The cDNA fragments covering the open reading frames for various chemokine receptors were obtained as follows. CCR4, CCR5 and CCR6 receptors were cloned from a K562 cell cDNA library by polymerase chain reaction (PCR). The primers were designed using the sequences from the following GenBank™ submissions: CCR4 (NM_005508.2), CCR5 (NM_000579) and CCR6 (AY242126). The fragments were cloned into an expression vector pcDI (modified in our lab from pcDNA3 vector (Invitrogen), in which the part between BgI II-Kpn I was replaced by the fragment of pCI vector (Promega) digested with BgI II-Kpn I) or pEGFP-N1 vector (CLONTECH) for efficient expression in HEK293 cells. The sequences coding receptors in expression plasmids were confirmed by DNA sequencing, which is consistent with the sequence submitted in GenBank™.

(ii). Cell Culture and Receptor Expression

HEK293 cells were grown in RPMI 1640 supplemented with 10% heat-inactivated FBS, penicillin (100 U/ml) and streptomycin (100 μg/ml). Every $4 \times 10^6$ HEK293 cells in 400 μl were transiently transfected by electroporation with 15 μg of the expression plasmid at 120 V, 20 ms using an electric pulse generator (Electro Square Porator ECM 830, BTX, San Diego, Calif.), and calcium mobilization assay and chemotaxis assays were performed 48 hours later.

Figure 7A:
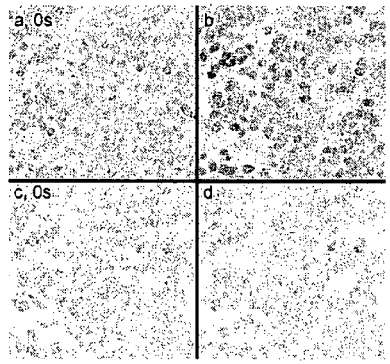
FIGS. 7A-7H show calcium flux assays. The cognate ligand for CCR4 was TARC; and for CCR5 was RANTES. Monolayers of HEK293 cells were transiently transfected with CCR4 expression plasmid (FIGS. 7A-7D), or CCR5 expression plasmid FIGS. 7E-7H). Images were captured before and after stimulation.

2. Results:

In calcium mobilization assays or chemotaxis assays, the cognate ligand, TARC or RANTES (peprotech), was added into the supernatant of cells transfected with its corresponding receptor and induced the response of calcium mobilization or chemotaxis as shown the positive controls in FIGS. 7A thru 12. The FIGS. 7A-7H show calcium flux assays. The cognate ligand for CCR4 was TARC; and for CCR5 was RANTES. Monolayers of HEK293 cells were transiently transfected with CCR4 expression plasmid (FIGS. 7A-7D), or CCR5 expression plasmid (FIGS. 7E-7H). Images were captured before and after stimulation. In FIG. 7A, cells were first stimulated with 100 nM TARC (a-b) and secondly stimulated with 167 nM C27 (c-d); in FIG. 7B, cells were first stimulated with 167 nM C27 (a-b) and secondly stimulated with 100 nM TARC (c-d); in FIG. 7C, cells were first stimulated with 100 nM TARC (a-b) and secondly stimulated with 167 nM C19 (c-d); in FIG. 7D, cells were first stimulated with 167 nM C19 (a-b) and secondly stimulated with 100 nM TARC (c-d); in FIG. 7E, cells were first stimulated with 100 nM RANTES (a-b) and secondly stimulated with 167 nM C27 (c-d); in FIG. 7F cells were first stimulated with 167 nM C27 (a-b) and secondly stimulated with 100 nM RANTES (c-d); in FIG. 7G, cells were first stimulated with 100 nM RANTES (a-b) and secondly stimulated with 167 nM C19 (c-d); and in FIG. 7H, cells were first stimulated with 167 nM C19 (a-b) and secondly stimulated with 100 nM RANTES (c-d).

Example 7

C27 and C19 Induce Cell Calcium Flux in CCR4 and CCR5 Transfected Cells

1. Methods:

HEK293 cells transfected with pcDI-CCR4 or pcDI-CCR5 were grown in specialized glass-bottom microwell dishes (MatTek Corporation, U.S.A.) and loaded with 10 μM fluo-3/AM in HEPES-buffered saline at 37° C. for 1 hour in the dark. The cells were rinsed with HEPES-buffered saline and stimulated with 167 nM secreted CKLF1 peptides and 100 nM TARC or RANTES, respectively. Fluorescence was monitored at 488 nm (excitation wavelength) and 530 nm (emission wavelength) every 5 second using a Leica TCS-NT confocal fluorescence microscope with a 40× oil immersion lens (Wetzler, Heidelberg, Germany). The measurement was completed at room temperature and each field of cells was selected at random. Images were collected at 5 second intervals for 405 seconds. The images were analyzed for relative fluorescence using Leica confocal software. The relative fluorescence was determined using Microsoft Excel. All calcium flux assays were performed in the presence of extracellular calcium (in the absence of EDTA or EGTA) in the assay buffers. Therefore, both intracellular calcium release and extracellular calcium influx were analyzed.

Figure 7B:
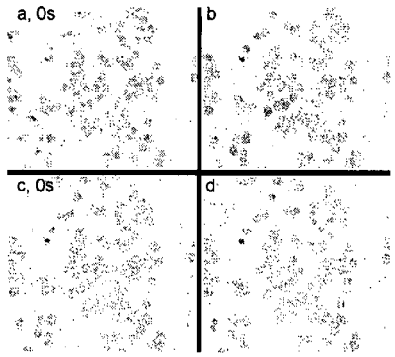
Figure 7C:
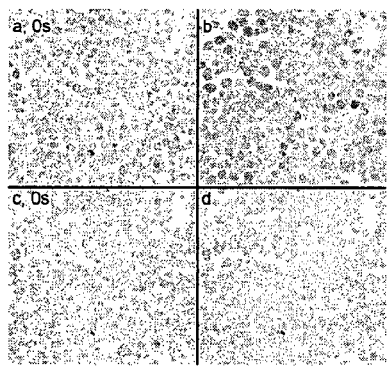
Figure 7D:
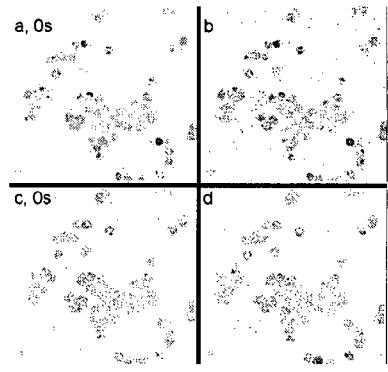
Figure 7E:
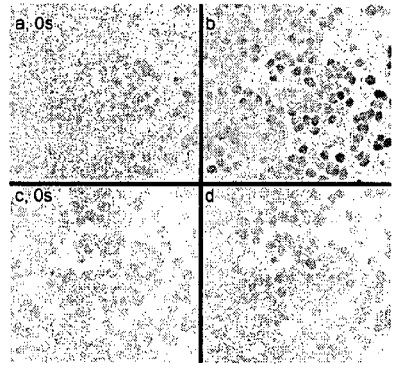
Figure 7F:
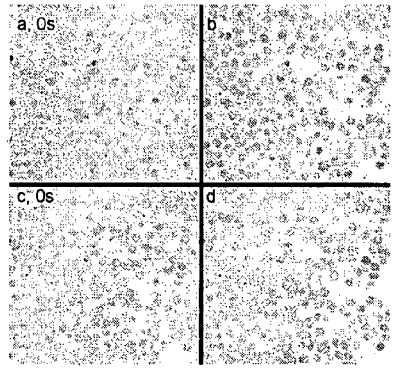
Figure 7G:
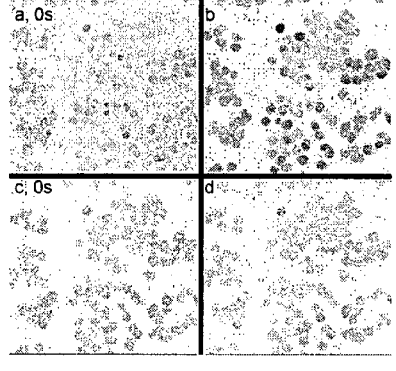
Figure 7H:
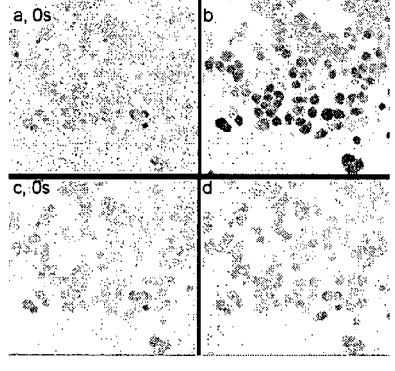
Figure 8A:
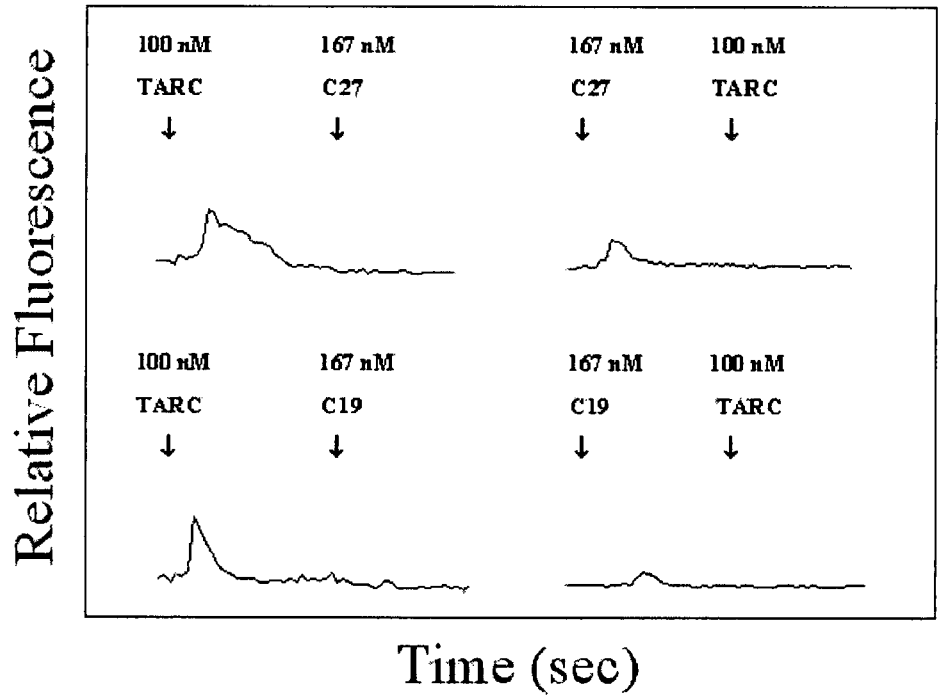
FIGS. 8A and 8B show the relative fluorescence from the images of calcium flux assays estimated with Leica confocal software.
Figure 8B:
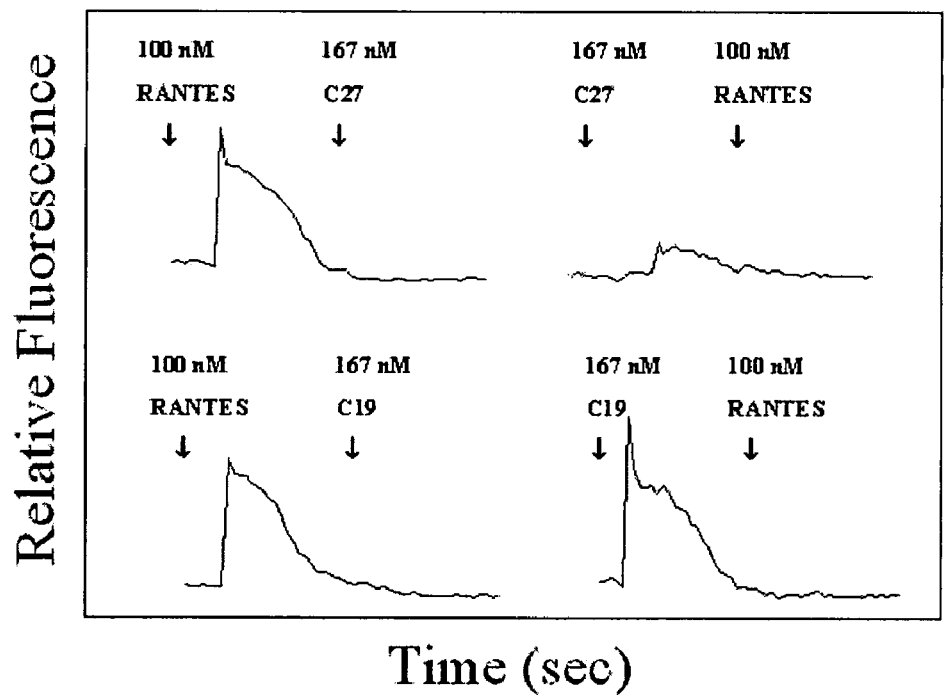

2. Results:

As shown in FIGS. 7A-7H, 8A and 8B, the cognate ligand for CCR4 was TARC; for CCR5 was RANTES. Monolayers of HEK293 cells were transiently transfected with CCR4 expression plasmid FIGS. A-7D), and CCR5 expression plasmid FIGS. 7E-7H). Images were captured before and after stimulation. The images shown in FIGS. 7A-7H were further described as follows: FIG. 7A, cells were first stimulated with 100 nM TARC (a-b) and secondly stimulated with 167 nM C27 (c-d); FIG. 7B, cells were first stimulated with 167 nM C27 (a-b) and secondly stimulated with 100 nM TARC (c-d); FIG. 7C, cells were first stimulated with 100 nM TARC (a-b) and secondly stimulated with 167 nM C19 (c-d); FIG. 7D, cells were first stimulated with 167 nM C19 (a-b) and secondly stimulated with 100 nM TARC (c-d); FIG. 7E, cells were first stimulated with 100 nM RANTES (a-b) and secondly stimulated with 167 nM C27 (c-d); FIG. 7F, cells were first stimulated with 167 nM C27 (a-b) and secondly stimulated with 100 nM RANTES (c-d); FIG. 7G, cells were first stimulated with 100 nM RANTES (a-b) and secondly stimulated with 167 nM C19 (c-d); FIG. 7H, cells were first stimulated with 167 nM C19 (a-b) and secondly stimulated with 100 nM RANTES (c-d). The relative fluorescence from the images of calcium flux assays was estimated with Leica confocal software as shown in FIGS. 8A and 8B. In FIG. 8A, cells were transiently transfected with CCR4 expression plasmid. In FIG. 8B, cells were transiently transfected with CCR5 expression plasmid.

TARC or RANTES induced calcium flux in HEK293 cells expressing their cognate receptor. C27 and C19 could induce calcium flux in CCR4-transfected HEK293 cells and a strong calcium flux in CCR5-transfected HEK293 cells. C27 and C19 could desensitize CCR4 or CCR5 transfectants to subsequent TARC or RANTES treatment, though the lower intensity signal was produced by initial C27 in CCR4 or CCR5 transfectants, or by initial C19 in CCR4 transfectants. In the same way, pretreatment with TARC or RANTES also desensitized the receptor to subsequent stimulation with C27 and C19. These results clearly demonstrate that C27 and C19 can interact with CCR4 and CCR5.

Example 8

Chemotactic Activity of C27 and C19

1. Methods:

The chemotaxis assay was performed using a 48-well microchemotaxis chamber (Neutroprobe; Cabin John, Md., U.S.A.). Chemoattractants were diluted in HEPES-buffered RPMI 1640 medium supplemented with 0.1% BSA and placed in the lower wells (28 μl/well). HEK293 cells transfected with pcDI-CCR4, -CCR5 were resuspended in the same medium at $2\times10^6$ cells/ml and added to the upper wells (50 μl/well), which were separated from the lower wells by a polyvinylpyrrolidone-free polycarbonate filter with 8-μm pores. The chamber was incubated for 2 hours at 37° C. in 5% $CO_2$ and 95% air. Filters were removed from the chamber, washed, fixed, and stained with Three Step Stain Set. Cells that migrated were counted in 5 randomly selected high power fields (400×) per well. The chemotactic index (CI) was calculated from the number of cells that migrated to the control. Significant chemotaxis was defined as CI>2. In some experiments, cells were pretreated with TARC, RANTES, purified CKLF-myc protein or secreted CKLF1 peptides for 30 min. at 37° C., or 100 ng/ml PTX (ALEXIS Biochemicals Corporation) for 6 hours at 37° C. prior to subsequent stimulations.

Figure 9A:
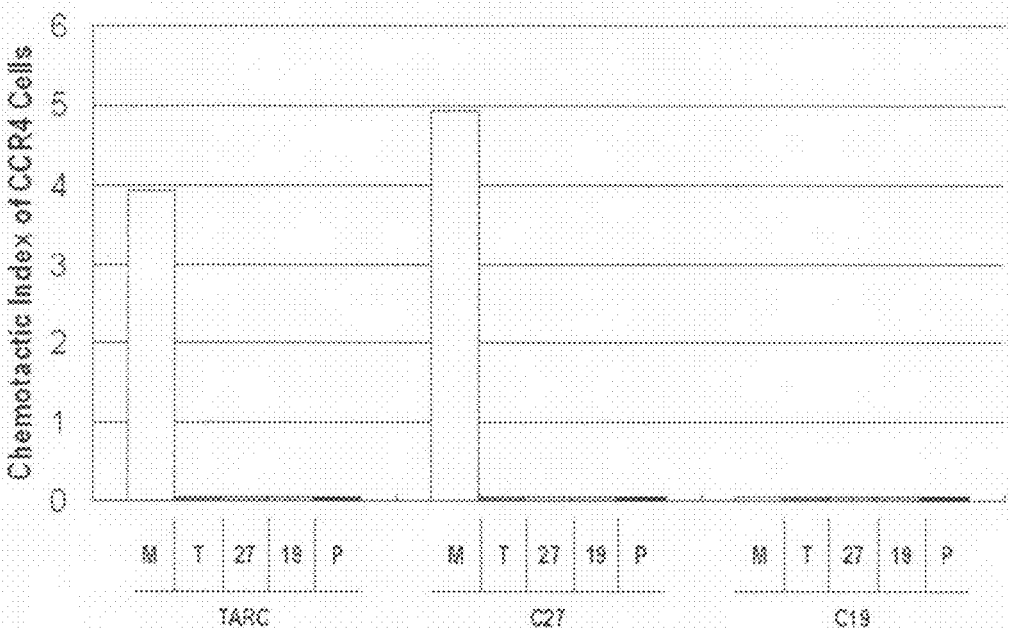
FIGS. 9A and 9B show chemotaxis of CCR4 or CCR5 transfectants to CKLF1 C-terminal peptides, TARC or RANTES. Cells were placed in upper wells and C27, C19, TARC or RANTES in the lower wells.
Figure 9B:
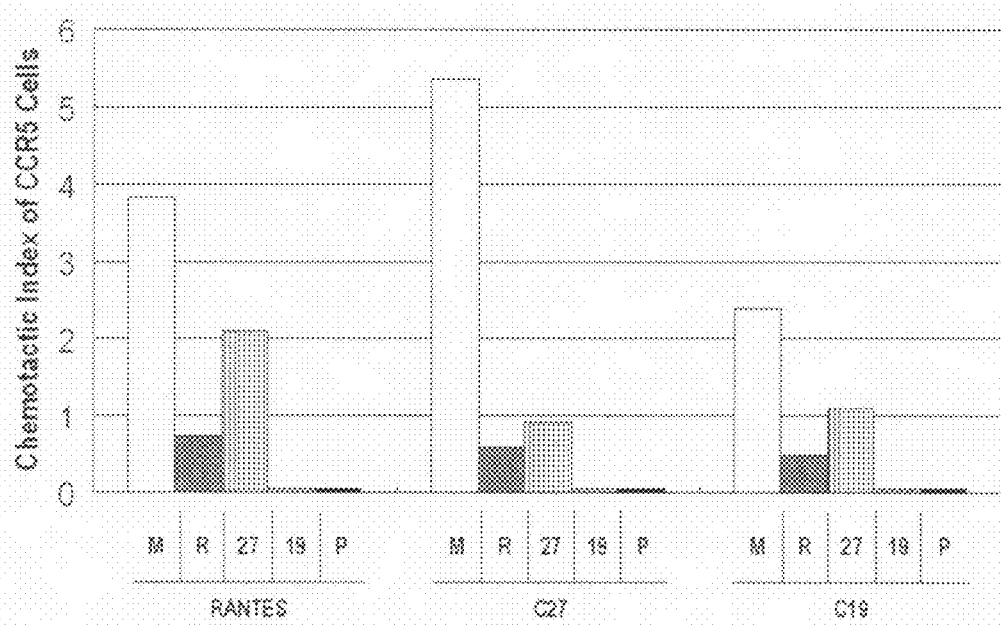

2. Results:

As shown in FIG. 9A, chemotaxis of HEK293 cells transfected with CCR4. HEK293/CCR4 cells were pre-incubated in the absence or presence of CKLF1 C-terminal peptides, TARC or PTX for 30 min; in FIG. 9B, HEK293/CCR5 cells were pre-incubated in the absence or presence of CKLF1 C-terminal peptides, RANTES or PTX for 30 min., wherein M is RPMI-1640; T is TARC; 27 is C27; 19 is C19; P is PTX; and R is RANTES. C27 could induce migration of CCR4 or CCR5-transfected HEK293 cells. The pretreatment with 1 mM TARC or RANTES, or with 2 μg/ml C27 or C19 at 37° C. for 30 min could desensitize the receptor to subsequent stimulation with TARC or RANTES, C27 or C19. To evaluate whether C27 or C19 exerts its effect through a receptor linked to a PTX-sensitive Gi/Go family G proteins, CCR4 or CCR5-transfected HEK293 cells were treated with 100 ng/ml PTX at 37° C. for 30 min before the stimulation of C27, C19, TARC, or RANTES. The results showed that the chemotaxis induced by C27, C19, TARC, or RANTES completely abolished by PTX, suggesting the involvement of a Gi/o pathway (Oh, et al., 2002; New and Wong, 2003). These results further confirm that C27 and C19 can interact with CCR4 or CCR5.

Figure 11:
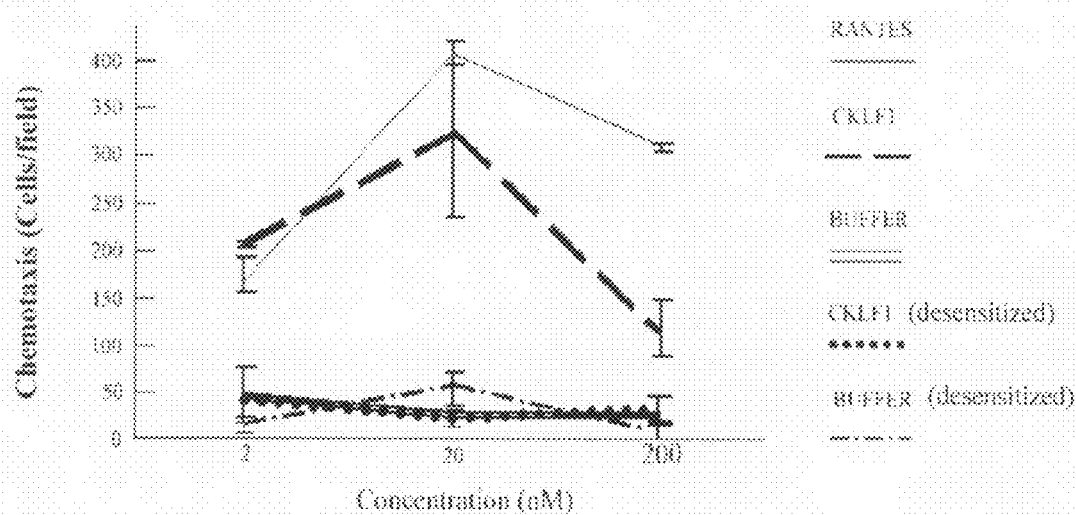
FIG. 11 shows the chemotaxis and chemotaxis desensitization of CCR4 transfectants to the purified CKLF1-myc protein.

As shown in FIG. 11, the purified CKLF1-myc protein could induce the chemotaxis of CCR4-transfected HEK293 and the pretreatment with RANTES could desensitize the receptor to subsequent stimulation with the purified CKLF1-myc protein, suggesting that the results from CKLF1 C-terminal peptides and purified CKLF1-myc protein were consistent.

Example 9

Internalization of CCR6 Receptor Induced by C27 and C19

1. Methods:

The cDNA fragment covering the open reading frame for CCR6 chemokine receptor was cloned into pEGFP-N1 vector (CLONTECH). pCCR6-EGFP transiently expressing HEK293 cells were cultured in glass-bottom dishes in RPMI 1640 with 10% FBS. After 16-24 hours of serum starvation, cells were treated with CKLF1 C-terminal peptides or MIP3α at 37° C. for 2 hours. Cells were washed with cold PBS and fixed with 2% paraformaldehyde in PBS. The subcellular localization of CCR6-EGFP protein was visualized using a Leica TCS-NT confocal fluorescence microscope with a 63× oil immersion lens (Wetzler, Heidelberg, Germany). The excitation and emission wavelengths were 488 and 515-540 nm, respectively.

Figure 12:
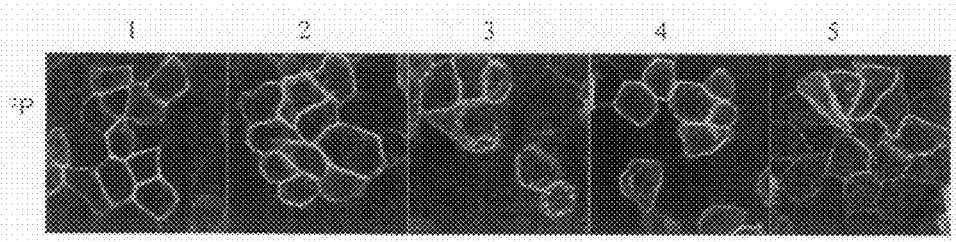
FIG. 12 shows internalization of chemokine receptors induced by MIP3α or CKLF1 peptides. HEK293 cells were transiently transfected with pCCR6-EGFP and then treated with the BSA (2), MIP3α (3), C27 (4) or C19 (5). Medium was a negative control (1), and BSA (2) was an unrelated protein control.

2. Results:

As shown in FIG. 12, HEK293 cells were transiently transfected with pCCR6-EGFP and then treated with the BSA (2), MIP3((3), C27 (4) or C19 (5). Medium was a negative control (1) and BSA (2) was an unrelated protein control. The results showed that C27 or C19 could induce internalization of CCR6-EGFP, suggesting that C27 or C19 could interact with CCR6.

Example 10

Anti-CKLF1 Antibody Preparation

1. Methods:

The CSGPYQKKPVHEKKEVL peptide derived from the human CKLF1 C-terminal, i.e., the 15 C-terminal amino acid peptides of C27 or C19 and a cysteine was added in its N-terminal for the coupling to KLH (Pierce).

Polyclonal anti-CKLF1 antibody was raised in 2.5 kg adult male New Zealand White rabbits primarily immuned with 1 mg KLH coupled polypeptide and Freund's complete adjuvant (FCA), then the immune response was strengthened with 1 mg KLH coupled polypeptide and Freund's incomplete adjuvant (FIA) at 21 days, 42 days, and 63 days, respectively.

2. Results:

7-10 days after the rabbit was immuned each time, the titer of the antibody in the serum was tested by ELISA, until it reached $1\times10^{-4}$. The serum was separated and the antibody was purified by Protein G affinity chromatography, and stored in 0.01M PBS.

Example 11

Internalization of CCR4 Receptor Induced by C27 and C19

1. Methods:

The cDNA fragment covering the open reading frame for CCR4 chemokine receptor was cloned into pEGFP-N1 vector (CLONTECH). pCCR4-EGFP transiently expressing HEK293 cells were cultured in glass-bottom dishes in RPMI 1640 with 10% FBS. After 16 to 24 hours serum starvation, cells were treated with CKLF1 C-terminal peptides or TARC at 37° C. for 2 hours. Cells were washed with cold PBS and fixed with 2% paraformaldehyde in PBS. The subcellular localization of CCR4-EGFP protein was visualized using a Leica TCS-NT confocal fluorescence microscope with a 63× oil immersion lens (Wetzler, Heidelberg, Germany). The excitation and emission wavelengths were 488 and 515-540 nm, respectively.

Figure 13:
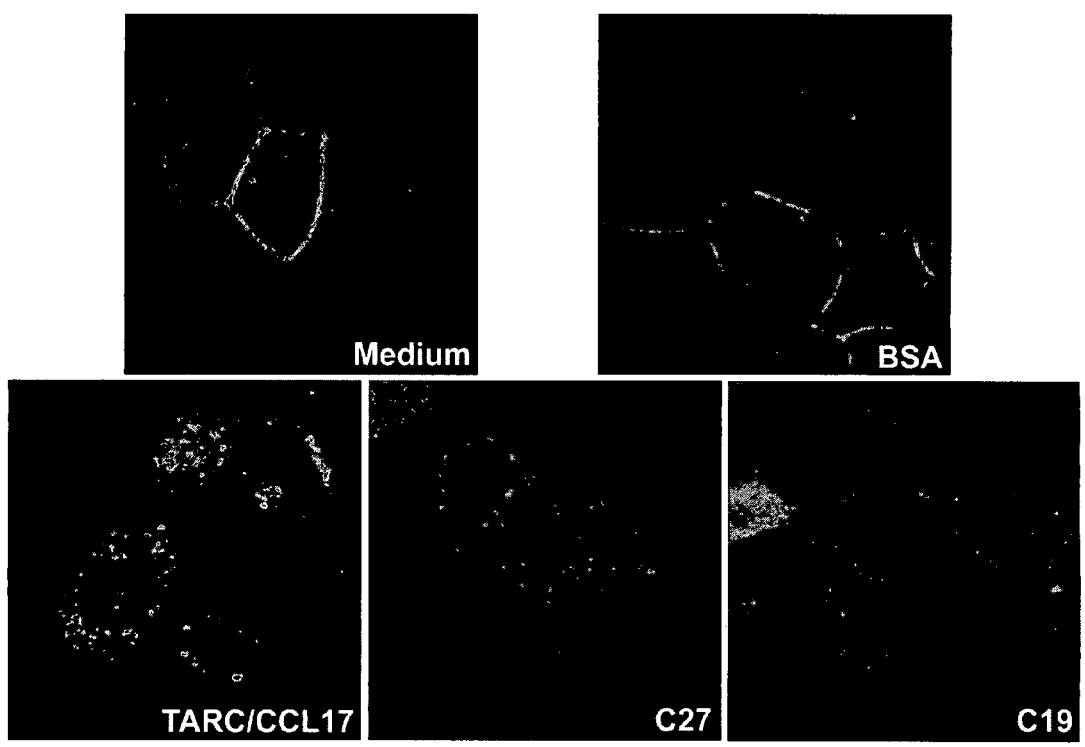
FIG. 13 shows internalization of chemokine receptors induced by TARC or CKLF1 peptides. HEK293 cells were transiently transfected with pCCR4-EGFP and then treated with the BSA, TARC, C27 or C19. Medium was a negative control, and BSA was an unrelated protein control.

2. Results:

As shown in FIG. 13, HEK293 cells were transiently transfected with pCCR4-EGFP and then treated with the BSA, TARC, C27 or C19. Medium was a negative control and BSA was an unrelated protein control. Result showed that C27 or C19 could induce internalization of CCR4-EGFP, suggesting that C27 or C19 can interact with CCR4.

Example 12

Chemotaxis in U937 cells

1. Methods

The chemotaxis assay was performed using a 48-well microchemotaxis chamber (Neutroprobe, Cabin John, Md., U.S.A.). U937 cells were stimulated by 30 ng/ml IFN-γ for 4 days because IFN-γ could increase the expression of chemokine receptors CCR1, CCR3, and CCR5 in U937 cells. Then part cells were incubated with mouse anti CCR5 100 μg/ml, and/or rat anti CCR3 10 μg/ml for 30 minutes at 37° C., and corresponding mouse IgG and rat IgG as controls. Chemoattractants RANTES, C19 and C27 were diluted in HEPES-buffered RPMI 1640 medium supplemented with 0.5% BSA to indicate concentration, and placed in the lower wells (28 μl/well). U937 cells stimulated by IFN-γ were resuspended in the same medium at $1 \times 10^6$ cells/ml and added to the upper wells (50 μl/well), which were separated from the lower wells by a polyvinylpyrrolidone-free polycarbonate filter with 5-μm pores pre-coated by 0.001% fibronectin. The chamber was incubated for 2 hours at 37° C. in 5% $CO_2$ and 95% air. Filters were removed from the chamber, washed, fixed, and stained with Three Step Stain Set. Cells that migrated were counted in 5 randomly selected high power fields (400×) per well. The group with no Chemoattractants in the lower wells was used as a control. All samples were assayed twice at least. The chemotactic index (CI) was calculated from the number of cells that migrated to the control. Significant chemotaxis was defined as CI>2.

Figure 14:
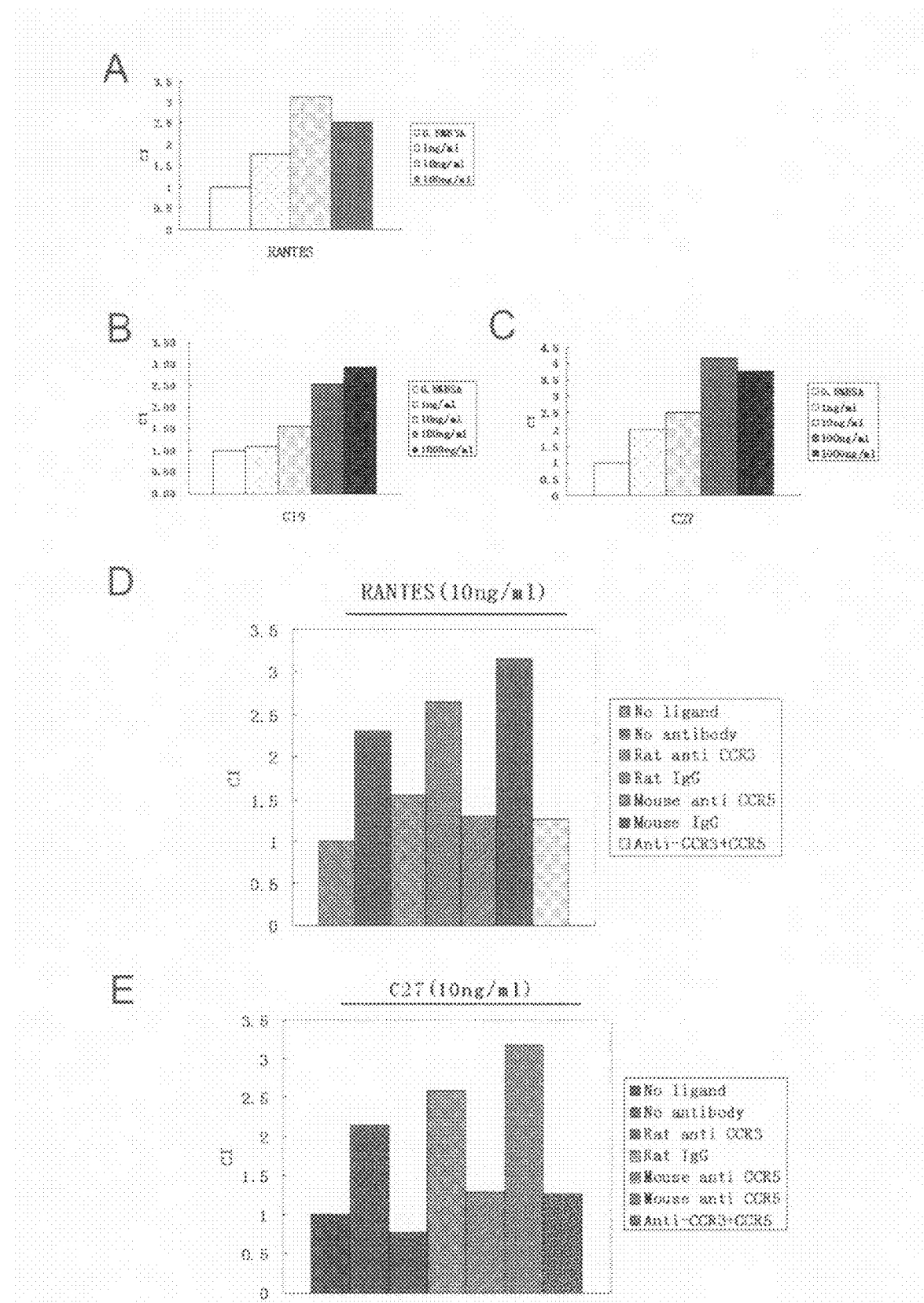
FIG. 14 shows chemotaxis of U937 cells to CKLF1 C-terminal peptides. RANTES (A), C19 (B) and C27 (C) could induce migration of U937 cells stimulated by IFN-γ, and when the chemokine receptors were neutralized by mouse anti CCR5 and/or rat anti CCR3, the chemotactic activity of RANTES (D) or C27 (E) was obviously inhibited. RANTES was a positive control (A and D).

2. Results:

The present invention used U937 cells stimulated by 30 ng/ml IFN-γ, which could increase the expression of chemokine receptors CCR1, CCR3, and CCR5, to test whether C27 had chemotactic activity to CCR1, CCR3, and CCR5, especially to test whether it had chemotactic activity to chemokine receptors constitutively expressed in cells. As shown in the bar graph in FIG. 14, C19 (B) and C27 (C) could induce migration of U937 cells stimulated by IFN-γ, and when the chemokine receptors were neutralized by mouse anti CCR5 and/or rat anti CCR3, C27 had no chemotactic activity to the cells (E). RANTES was a positive control (A and D).

Figure 10:
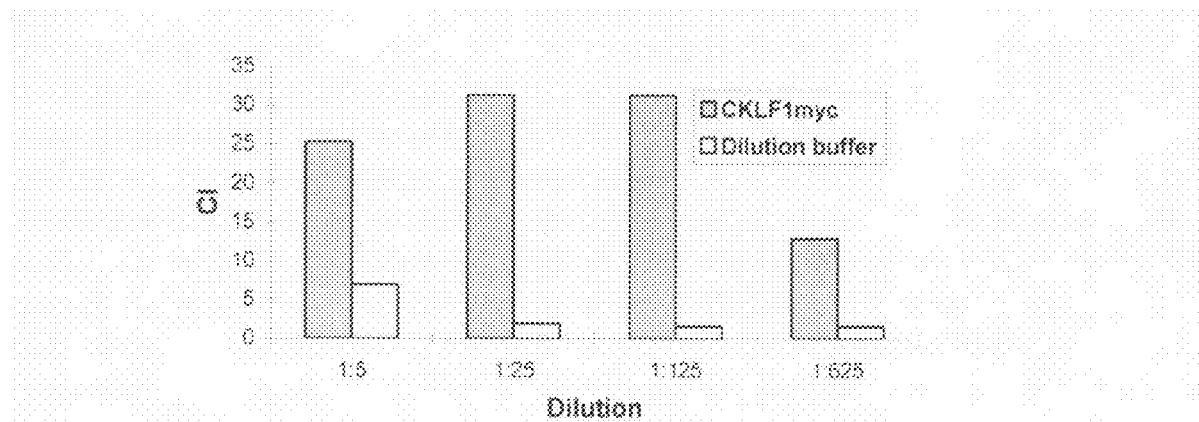
FIG. 10 shows chemotaxis of U937 cells to the purified CKLF1-myc protein.

As shown in FIG. 10, the purified CKLF1-myc protein can induce the chemotaxis of U937 cells.

Example 13

C19 Treatment Inhibits Airway Inflammation in the OVA-Sensitized Murine Asthma Model 1. Methods:

C57BL/6 mice (20-25 g) of either sex were sensitized by an i.p. injection (100 μl) of 20 μg chicken OVA (Sigma-Aldrich, St. Louis, Mo.) emulsified in Imject alum (2.25 mg Al $(OH)_3$/2 mg $Mg(OH)_2$) (Pierce, Rockfield, Ill.) on days 0 and 14. Mice were injected with 1, 10, or 100 μg of C27 or C19 i.p, and thirty minutes later, these mice were subsequently challenged with an aerosol generated from 1% OVA in saline (OVA), or saline alone, for 20 min by ultrasonic nebulization (DeVilbiss, Somerset, Pa.). This procedure was repeated daily on days 24, 25, and 26. The mice were assessed on day 28.

2. Results:

Pretreatment with C19 at doses ranging from 1 to 100 μg/mouse significantly demonstrated 78, 69 and 74% inhibition of eosinophil recruitment into the airways as assessed by BAL fluid analysis, compared with the positive control group. On the contrary, pretreatment with C27 at doses ranging from 1 to 100 μg/mouse did not demonstrate any inhibition of the eosinophil infiltration into the BAL fluid compared with the positive control group.

In the C19-treated group, a significant decrease was observed in airway hyperreactivity. The administration of C27 caused a small, but not statistically significant, increase in airway hyperreactivity.

What is claimed is:

1. An isolated polypeptide comprising: (a) the amino acid sequence of SEQ ID NO: 2; (b) amino acid residues 9 to 27 of SEQ ID NO: 2; (c) the amino acid sequence encoded by the polynucleotide of SEQ ID NO: 1; or (d) the amino acid sequence encoded by the nucleotides 25 to 81 of SEQ ID NO: 1.

2. A fusion protein, consisting of the polypeptide of claim 1 and a peptide tag.

3. The fusion protein of claim 2, wherein the peptide tag is myc or myc-his6.

4. A pharmaceutical composition comprising the polypeptide of claim 1(*b*) or 1(*d*) and one or more pharmaceutically acceptable salts, carriers or excipients.

5. A composition comprising the polypeptide of claim 1 and one or more pharmaceutically acceptable salts, carriers, or excipients.

6. A method of treating asthma comprising administering an effective amount of the pharmaceutical composition of claim 4 to a mammal suffering from asthma.

7. An isolated polypeptide consisting of an amino acid sequence having at least 90% sequence identity to: a) the amino acid sequence of SEQ ID NO: 2; (b) amino acid residues 9 to 27 of SEQ ID NO: 2; (c) the amino acid sequence encoded by the polynucleotide of SEQ ID NO: 1; or (d) the amino acid sequence encoded by nucleotides 25 to 81 of SEQ ID NO: 1.

8. An isolated polypeptide consisting of an amino acid sequence having at least 95% sequence identity to: a) the amino acid sequence of SEQ ID NO: 2; (b) amino acid residues 9 to 27 of SEQ ID NO: 2; (c) the amino acid sequence encoded by the polynucleotide of SEQ ID NO: 1; or (d) the amino acid sequence encoded by nucleotides 25 to 81 of SEQ ID NO: 1.

* * * * *

SEQUENCE LISTING

```
<160> NUMBER OF SEQ ID NOS: 10

<210> SEQ ID NO 1
<211> LENGTH: 81
<212> TYPE: DNA
<213> ORGANISM: Homo sapiens
<220> FEATURE:
<221> NAME/KEY: CDS
<222> LOCATION: (1)..(81)
<223> OTHER INFORMATION:

<400> SEQUENCE: 1 gcc ctt att tac cgg aag ctt ctg ttc aat ccc agc ggt cct tac cag      48
Ala Leu Ile Tyr Arg Lys Leu Leu Phe Asn Pro Ser Gly Pro Tyr Gln
1               5                   10                  15 aaa aag cct gtg cat gaa aaa aaa gaa gtt ttg                          81
Lys Lys Pro Val His Glu Lys Lys Glu Val Leu
            20                  25

<210> SEQ ID NO 2
```

```
<211> LENGTH: 27
<212> TYPE: PRT
<213> ORGANISM: Homo sapiens

<400> SEQUENCE: 2

Ala Leu Ile Tyr Arg Lys Leu Leu Phe Asn Pro Ser Gly Pro Tyr Gln
1               5                   10                  15

Lys Lys Pro Val His Glu Lys Lys Glu Val Leu
            20                  25

<210> SEQ ID NO 3
<211> LENGTH: 310
<212> TYPE: DNA
<213> ORGANISM: Homo sapiens

<400> SEQUENCE: 3
agacgcgatg gataacgtgc agccgaaaat aaaacatcgc cccttctgct tcagtgtgaa        60
aggccacgtg aagatgctgc ggctggatat tatcaactca ctggtaacaa cagtattcat       120
gctcatcgta tctgtgttgg cactgatacc agaaccaca  acattgacag ttggtggagg       180 ggtgttttgca cttgtgacag cagtatgctg tcttgccgac ggggccctta tttaccggaa      240
gcttctgttc aatcccagcg gtccttacca gaaaaagcct gtgcatgaaa aaaagaagt       300 tttgtaattt                                                              310

<210> SEQ ID NO 4
<211> LENGTH: 20
<212> TYPE: DNA
<213> ORGANISM: artificial sequence
<220> FEATURE:
<223> OTHER INFORMATION: primer

<400> SEQUENCE: 4
tgtaatacga ctcactatag                                                    20

<210> SEQ ID NO 5
<211> LENGTH: 26
<212> TYPE: DNA
<213> ORGANISM: artificial sequence
<220> FEATURE:
<223> OTHER INFORMATION: primer

<400> SEQUENCE: 5
cattgagttt aaacggtctc gagcgg                                             26

<210> SEQ ID NO 6
<211> LENGTH: 23
<212> TYPE: DNA
<213> ORGANISM: artificial sequence
<220> FEATURE:
<223> OTHER INFORMATION: primer

<400> SEQUENCE: 6
atggataacg tgcagccgaa aat                                                23

<210> SEQ ID NO 7
<211> LENGTH: 25
<212> TYPE: DNA
<213> ORGANISM: artificial sequence
<220> FEATURE:
<223> OTHER INFORMATION: primer

<400> SEQUENCE: 7
caaaacttct tttttttcat gcaca                                              25
```

```
<210> SEQ ID NO 8
<211> LENGTH: 19
<212> TYPE: DNA
<213> ORGANISM: artificial sequence
<220> FEATURE:
<223> OTHER INFORMATION: primer

<400> SEQUENCE: 8
gcaagaagcg ggaagccga                                                19

<210> SEQ ID NO 9
<211> LENGTH: 20
<212> TYPE: DNA
<213> ORGANISM: artificial sequence
<220> FEATURE:
<223> OTHER INFORMATION: primer

<400> SEQUENCE: 9
accacagtcc atgccatcac                                               20

<210> SEQ ID NO 10
<211> LENGTH: 20
<212> TYPE: DNA
<213> ORGANISM: artificial sequence
<220> FEATURE:
<223> OTHER INFORMATION: primer

<400> SEQUENCE: 10
tccaccaccc tgttgctgta                                               20
```